United States Patent [19]

Mao

[11] Patent Number: 4,483,979

[45] Date of Patent: Nov. 20, 1984

[54] POLAR SOLVENT EXTRACTION OF COLORED MATERIALS FROM ALKYLSACCHARIDES UNDER ESSENTIALLY ANHYDROUS CONDITIONS

[75] Inventor: Mark H. K. Mao, Cincinnati, Ohio

[73] Assignee: The Procter & Gamble Company, Cincinnati, Ohio

[21] Appl. No.: 447,902

[22] Filed: Dec. 8, 1982

[51] Int. Cl.$^3$ .............................................. C07H 1/00
[52] U.S. Cl. .................... 536/18.6; 536/4.1; 536/18.5; 536/127; 536/124
[58] Field of Search ............... 536/4.1, 18.6, 124, 536/127, 18.5, 119

[56] References Cited

U.S. PATENT DOCUMENTS

| | | | |
|---|---|---|---|
| 2,258,168 | 10/1941 | White | 536/4.1 |
| 2,552,896 | 5/1951 | Lee et al. | 536/4.1 |
| 2,682,533 | 6/1954 | Davy | 536/18.5 |
| 2,715,121 | 8/1955 | Glen et al. | 536/4.1 |
| 2,948,716 | 8/1960 | Davis | 536/119 |
| 3,378,542 | 4/1968 | O'Boyle | 536/119 |
| 3,378,544 | 4/1968 | O'Boyle | 536/119 |
| 3,384,634 | 5/1968 | O'Boyle | 536/119 |
| 3,715,402 | 2/1973 | Louvar et al. | 536/120 |
| 4,334,061 | 6/1982 | Bossier | 536/119 |
| 4,349,669 | 9/1982 | Klahr et al. | 536/124 |
| 4,393,203 | 7/1983 | Mao et al. | 536/124 |

*Primary Examiner*—Johnnie R. Brown
*Attorney, Agent, or Firm*—Robert B. Aylor; Richard C. Witte; Thomas H. O'Flaherty

[57] ABSTRACT

A process for removing colored materials from alkylpolysaccharides by extracting the colored materials with polar solvents under essentially anhydrous conditions.

21 Claims, No Drawings

POLAR SOLVENT EXTRACTION OF COLORED MATERIALS FROM ALKYLSACCHARIDES UNDER ESSENTIALLY ANHYDROUS CONDITIONS

BACKGROUND OF THE INVENTION

The preparation of alkylsaccharides via the acid catalyzed reaction of an alcohol and a reducing sugar containing either 5 or 6 carbon atoms, is well known. Examples of patents disclosing such processes include U.S. Pat. No. 3,598,865, Lew, patented Aug. 10, 1971; U.S. Pat. No. 3,219,656, Boettner, patented Nov. 23, 1965; U.S. Pat. No. 3,346,558, Roth, patented Oct. 10, 1967; U.S. Pat. No. 3,547,828, Mansfield et al, patented Dec. 15, 1970; U.S. Pat. No. 3,707,535, Lew, patented Dec. 16, 1972; U.S. Pat. No. 3,772,269, Lew, patented Nov. 13, 1973; U.S. Pat. No. 3,839,318, Mansfield, patented Oct. 1, 1974; and U.S. Pat. No. 4,223,129, Roth et al, patented Sept. 16, 1980, all of said patents being incorporated herein by reference. In all of these processes, colored materials are formed.

Various approaches to cleaning up the alkylsaccharides have been disclosed including extraction of the desired material. U.S. Pat. No. 2,258,168, White, patented Oct. 7, 1941; U.S. Pat. No. 2,715,121, Glenn et al, patented Aug. 9, 1965; and U.S. Pat. No. 3,450,690, Gibbons et al, patented June 17, 1969, disclose methods for removal of color producing bodies by extracting the desired product. U.S. Pat. No. 3,839,318, Mansfield, patented Oct. 1, 1974, discloses a process for bleaching the colored materials using perborate. All of the above patents are incorporated herein by reference.

SUMMARY OF THE INVENTION

This invention relates to the process of removing colored materials from alkylsaccharides by extracting the colored materials with a polar solvent under essentially anhydrous conditions.

DETAILED DESCRIPTION OF THE INVENTION

Polar Solvent

Polar solvents useful in the extraction process should have a boiling point between about 30° C. and about 200° C., preferably between about 45° C. and about 150° C., and have a dipole moment of greater than about 1.0, preferably greater than about 1.2 and less than about 4, preferably less than about 3, more preferably less than about 2.5. Suitable solvents include tetrahydrofuran, acetone, di-N-propyl ether, dioxane, bis-2-methoxyethyl ether, dimethyl sulfoxide, dimethyl sulfone, di-N-propyl sulfone, dibutyl oxide, bis-2-methoxyethyl ether (Diglyme), nitrobenzene, acetonitrile, formamide, dimethyl formamide, methyl ethyl ketone, diethyl ketone, butyl aldehyde, ethyl acetate, propyl acetate, ethyl cellulose, butyl cellulose, chloroform, methylene chloride, freon, tetrachloro ethylene, and mixtures thereof. The preferred solvents are acetone, ethyl acetate, methyl ethyl ketone, diethyl ketone, and mixtures thereof. Mixtures of the above compounds with nonpolar solvents are also suitable and even desirable.

It is important that the solvent be anhydrous, i.e., it should contain less than about 2%, most preferably less than about 0.5% water. Also, it preferably should be nontoxic and be readily distilled to remove it from the colored materials.

The Alkylsaccharide

The alkylsaccharide is any compound in which the alkyl group is attached through the number one carbon atom of a 5- or 6-member reducing saccharide to said saccharide, or a polysaccharide chain. The compounds are formed by the reaction between an alcohol and a 5- or 6-membered reducing saccharide or source thereof. The alcohol can be either aliphatic or aromatic, or mixed aliphatic and aromatic, containing from 1 to about 32 carbon atoms, preferably from about 8 to about 24, most preferably from about 12 to about 18, and the saccharide portion of the molecule can contain from about 1 to about 50 saccharide monomers on the average. Such compounds are formed in the presence of acid catalysts, usually with the application of heat. Such compounds and the processes for making such compounds are well known and described in the patents incorporated hereinbefore.

Preferred compounds are those having a hydrophobic group containing from about 8 to about 20 carbon atoms, preferably from about 10 to about 16 carbon atoms, most preferably from 12 to 14 carbon atoms, and a polysaccharide hydrophilic group containing from about 1.5 to about 10, preferably from 1.5 to 4, most preferably from 1.6 to 2.7 saccharide units (e.g., galactoside, glucoside, and/or fructoside, units). Mixtures of saccharide moieties can be present in the alkyl polysaccharide surfactants. For a particular alkylpolysaccharide molecule the number of saccharide units (X) can only assume integral values. In any physical sample of alkylpolysaccharide surfactants there will, in general, be molecules having different X values. The physical sample can be characterized by the average value of X and this average value can assume non-integral values. In this specification the values of X are to be understood to be average values.

Optionally and less desirably there can be a polyalkoxide chain joining the hydrophobic moiety (R) and the polysaccharide-chain. The preferred alkoxide moiety is ethoxide.

Typical hydrophobic groups include alkyl groups, either saturated or unsaturated, branched or unbranched, containing from about 8 to about 20, preferably from about 10 to about 16 carbon atoms. Preferably, the alkyl group is a straight chain saturated alkyl group. The alkyl group can contain up to 3 hydroxy groups and/or the polyalkoxide chain can contain up to about 30, preferably less than 10, most preferably 0, alkoxide moieties.

Suitable alkyl polysaccharides are decyl, dodecyl, tetradecyl, hexadecyl, and octadecyl, di-, tri-, tetra-, penta-, and hexaglucosides, galactosides, lactosides, fructosides, and mixtures thereof.

The alkylmonosaccharides are relatively less soluble in water than the higher alkylpolysaccharides. When used in mixtures with alkylpolysaccharides, the alkylmonosaccharides are solubilized to some extent. The use of alkylmonosaccharides in mixtures with alkylpolysaccharides is preferred. Suitable mixtures include coconut alkyl, di-, tri-, tetra-, and pentaglucosides and tallow alkyl tetra-, penta-, and hexaglucosides.

The preferred alkyl polysaccharides are alkyl polyglycosides having the formula $$R^2O(C_nH_{2n}O)_t(Z)_x$$

wherein Z is derived from glucose, $R^2$ is a hydrophobic group selected from the group consisting of alkyl, alkylphenyl, hydroxyalkyl, hydroxyalkylphenyl, and mixtures thereof in which said alkyl groups contain from about 10 to about 18, preferably from 12 to 14 carbon atoms; n is 2 or 3, preferably 2; t is from 0 to about 10, preferably 0; and x is from 1.5 to about 8, preferably from 1.5 to 4, most preferably from 1.6 to 2.7. To prepare these compounds a long chain alcohol ($R^2OH$) can be reacted with glucose, or a compound hydrolyzable to glucose, in the presence of an acid catalyst to form the desired glycoside. Alternatively the alkylpolyglycosides can be prepared by a two step procedure in which a short chain alcohol ($C_{1-6}$) is reacted with glucose or a polyglycoside (x=2 to 4) to yield a short chain alkyl glycoside (x=1 to 4) which can in turn be reacted with a longer chain alcohol ($R^2OH$) to displace the short chain alcohol and obtain the desired alkylpolyglycoside. If this two step procedure is used, the short chain alkylglycoside content of the final alkylpolyglycoside material should be less than 50%, preferably less than 10%, more preferably less than 5%, most preferably 0% of the alkylpolyglycoside.

The amount of unreacted alcohol (the free fatty alcohol content) in the preferred alkylpolysaccharide surfactant is preferably less than about 2%, more preferably less than about 0.5% by weight of the total of the alkyl polysaccharide plus unreacted alcohol. The amount of alkylmonosaccharide is about 20% to about 70%, preferably 30% to 60%, most preferably 30% to 50% by weight of the total of the alkylpolysaccharide. For some uses it is desirable to have the alkylmonosaccharide content less than about 10%.

As used herein, "alkylpolysaccharide surfactant" is intended to represent both the preferred glucose and galactose derived surfactants and the less preferred alkylpolysaccharide surfactants. Throughout this specification, "alkylpolyglycoside" is used because the stereo chemistry of the saccharide moiety is changed during the preparation reaction.

The alkylsaccharides of this invention, as formed in the reaction, contain colored materials. It is important that the reaction mix not contain appreciable amounts of water. Preferably there should be less than about 2% water, and more preferably less than about 0.5% water, in the reaction mix. The invention allows the facile removal of the colored materials by a simple solvent extraction using from about 50% to about 1000%, preferably from about 100% to about 500%, more preferably from about 200% to about 300% of the polar solvent described hereinbefore. The solvent is mixed with the alkylsaccharide reaction mixture and then removed, typically by a simple decantation. Then, preferably, the solvent is boiled off and recycled.

The presence of more than about 10% water prevents the removal of the color bodies. In fact, once water is added to the reaction mixture, it is extremely difficult, or impossible, to extract the colored materials. Small amounts of nonpolar solvents are acceptable and even desirable, especially when it is desired to adjust the overall solvent polarity.

All parts, percentages, and ratios herein are by weight unless otherwise stated.

The following examples illustrate the practice of the invention.

EXAMPLE I

A dark colored reaction product mixture having a transmittance value of 2% at 470 nm in a 2 cm. cell, containing 45% alkyl polyglycosides and 55% Neodol 23 alcohol was mixed with 3 volumes of dry acetone having a dipole moment (polarity) of 2.8 and a boiling point of 56° C. A white precipitate formed from the brown colored acetone/fatty alcohol solution. This precipitate was collected by decantation and further washed with small amounts of acetone to remove residual solvents. The sediment was dried in a vacuum oven for 2 hours at 50° C. and 2 cm Hg pressure. The resulting cake was finely ground and used as surfactant without bleaching. The acetone solutions were distilled to recover the solvent. The residual fatty alcohol with some dissolved alkyl monoglucoside was recycled. A 45% solution in water of the product had a transmittance value of 33% at 470 nm in a 2 cm cell.

EXAMPLE II

A similar reaction mixture was washed with a 75/25 mixture of acetone and hexane, having a polarity of about 2.1 and boiling point between about 56° C. and about 64° C. This solvent mixture precipitates more of the alkyl monoglucoside than the 100% acetone.

EXAMPLE III

A 90/10 mixture of ethyl acetate and acetone, having a polarity of about 1.9 and boiling point between about 56° C. and about 68° C., was used in the procedure and generated material essentially the same in quality as in Example I.

EXAMPLE IV

The same reaction mixture was first distilled to remove most of the excess Neodol 23 using a Pope, 2 inch wiped film molecular still. The residual reaction mixture was then dissolved in one volume of hot hexane and then precipitated by adding 3 volumes of dry acetone giving the solvent mixture of Example II. The product was dried and gave a pure white powder.

EXAMPLE V

The 45/55 glycosides/fatty alcohol reaction mixture of Example I was washed with acetone with various amounts of water. The product yield was found to decrease when more than about 0.5% water is present in acetone.

EXAMPLE VI

The excess fatty alcohol of the reaction mixture of Example I was first removed through an Aldrich Kugelrohr distillation unit, Catalog No. Z10,046-3. The resulting product was ground into a fine powder which was dark brown in color. It was then extracted with dry acetone in a soxhlet extractor overnight. This completely removes the color bodies.

COMPARATIVE EXAMPLE VII

Triton BG-10, a 70% water solution of alkyl glycosides (Rohm & Haas product) was mixed with 3 volumes of acetone, no precipitate was formed. The presence of water changes the solvent polarity and dissolves the alkyl glycosides.

EXAMPLE VIII

The same reaction mixture of Example I was mixed with 2 volumes of dry acetone. The mixture was refluxed overnight. The solution of fatty alcohol in acetone was filtered. The residual reaction mixture was further washed with 0.5 volume of acetone and dried. This gave a cake with little color.

What is claimed is:

1. The process of removing colored materials which result from the preparation of alkyl saccharides by reacting an alcohol selected from the group consisting of aliphatic, aromatic and mixed aliphatic and aromatic alcohols containing from about 8 to about 24 carbon atoms with a 5- or 6-membered reducing saccharide or source thereof in the presence of an acid catalyst from said alkyl saccharides comprising extracting the colored materials with a polar solvent having a polarity of from about 1 to about 4, and a boiling point of from about 30° C. to about 200° C., the amount of polar solvent being from about 50% to about 1000% of said alkyl saccharides, and said solvent containing less than about 2% water.

2. The process of claim 1 wherein the polar solvent has a polarity of from 1.2 to about 3, and boils from about 45° C. to about 150° C., and the amount of solvent is from about 100% to about 500% of the alkyl saccharide.

3. The process of claim 2 wherein the solvent contains less than about 0.5% water.

4. The process of claim 1 wherein the solvent is selected from the group consisting of tetrahydrofuran, acetone, di-N-propyl ether, dioxane, bis-2-methoxyethyl ether, dimethyl sulfoxide, dimethyl sulfone, di-N-propyl sulfone, dibutyl oxide, bis-2-methoxyethyl ether, nitrobenzene, acetonitrile, formamide, dimethyl formamide, methyl ethyl ketone, diethyl ketone, butyl aldehyde, ethyl acetate, propyl acetate, ethyl cellulose, butyl cellulose, chloroform, methylene chloride, tetrachloro ethylene, and mixtures thereof.

5. The process of claim 4 wherein said solvent comprises a nonpolar solvent.

6. The process of claim 4 wherein the solvent contains less than about 0.5% water.

7. The process of claim 4 wherein the solvent comprises a material selected from the group consisting of acetone, ethyl acetate, methyl ethyl ketone, diethyl lactone, and mixtures thereof.

8. The process of claim 7 wherein the solvent contains less than about 0.5% water.

9. The process of claim 7 wherein the solvent is from about 200% to about 300% of the alkyl saccharide.

10. The process of claim 9 wherein the solvent contains less than about 0.5% water.

11. The process of claim 10 wherein the solvent's polarity is from about about 1.2 to about 3.

12. The process of claim 1 wherein in the alkyl saccharide the alkyl group contains from about 8 to 20 carbon atoms and the saccharide portion contains from about 1.5 to about 10 saccharide units on the average.

13. The process of claim 12 wherein said alkyl group contains from about 10 to about 16 carbon atoms and wherein the average number of saccharide units in the molecule is from about 1.5 to about 4.

14. The process of claim 13 wherein the polar solvent has a polarity of from 1.2 to about 3, and boils from about 45° C. to about 150° C., and the amount of solvent is from about 100% to about 500% of the alkyl saccharide.

15. The process of claim 14 wherein the solvent contains less than about 0.5% water.

16. The process of claim 13 wherein the solvent is selected from the group consisting of tetrahydrofuran, acetone, di-N-propyl ether, dioxane, bis-2-methoxyethyl ether, dimethyl sulfoxide, dimethyl sulfone, di-N-propyl sulfone, dibutyl oxide, bis-2-methoxyethyl ether, nitrobenzene, acetonitrile, formamide, dimethyl formamide, methyl ethyl ketone, diethyl ketone, butyl aldehyde, ethyl acetate, propyl acetate, ethyl cellulose, butyl cellulose, chloroform, methyl chloride from tetrachloro ethylene, and mixtures thereof.

17. The process of claim 16 wherein said solvent comprises a nonpolar solvent.

18. The process of claim 16 wherein the solvent contains less than about 0.5% water.

19. The process of claim 16 wherein the solvent comprises a material selected from the group consisting of acetone, ethyl acetate, methyl ethyl ketone, diethyl lactone, and mixtures thereof.

20. The process of claim 19 wherein the solvent contains less than about 0.5% water.

21. The process of claim 19 wherein the solvent is from about 200% to about 300% of the alkyl saccharide.

* * * * *